United States Patent [19]

Bischofberger et al.

[11] Patent Number: 5,175,273

[45] Date of Patent: Dec. 29, 1992

[54] NUCLEIC ACID INTERCALATING AGENTS

[75] Inventors: Norbert W. Bischofberger, San Carlos; Mark D. Matteucci, Burlingame, both of Calif.

[73] Assignee: Genentech, Inc., South San Francisco, Calif.

[21] Appl. No.: 213,957

[22] Filed: Jul. 1, 1988

[51] Int. Cl.$^5$ .................. C07H 19/073; C07H 21/04; C07H 15/18

[52] U.S. Cl. ........................ 536/27; 536/11; 536/18.7; 536/22; 536/23; 536/28; 536/29

[58] Field of Search ............... 536/27, 28, 29, 1.1, 536/18.7, 22, 23; 435/6

[56] References Cited

U.S. PATENT DOCUMENTS

| | | | |
|---|---|---|---|
| 3,893,998 | 7/1975 | Secrist et al. | 536/29 |
| 4,277,466 | 7/1981 | Trouet | 424/180 |
| 4,373,071 | 2/1983 | Itakura | 525/375 |
| 4,547,569 | 10/1985 | Letsinger et al. | 536/27 |
| 4,797,480 | 1/1989 | Sorbi et al. | 536/27 |
| 4,835,263 | 5/1989 | Nguyen et al. | 536/27 |

FOREIGN PATENT DOCUMENTS 0324616 7/1989 European Pat. Off.

OTHER PUBLICATIONS

Stryer, Biochemistry, 3rd Ed., W H Freeman & Co, N.Y., pp. 654-655.

Alberts et al., Molecular Biology of the Cell, pp. 95-96, 98-99 2nd ed., Garland Publishing, Inc., New York & London.

Watson et al., Molecular Biology of the Gene, 4th ed., Benjamin/Cummings Publishing Co., Inc., Menlo Park, Calif., pp. 254-255.

Morrison & Boyd, Organic Chemistry, 4th ed., Allyn and Bacon, Inc., Mass., pp. 1249-1251, 1284-1285.

Aldrich Fine Chemicals, Aldrich Chemical Co., Inc. (1986) p. 1411.

The Merck Index, 10th ed., Martha Windholz, editor, [pp. ONR-84, ONR-15, 1021,] Merck & Co., Inc., Rahway, N.J. (1983), 158, 150, 159.

*Primary Examiner*—Johnnie R. Brown
*Assistant Examiner*—Gary L. Kunz
*Attorney, Agent, or Firm*—Daryl B. Winter; Max D. Hensley

[57] ABSTRACT

Pyridinone or pyrimidinone nucleoside bases containing fused aromatic polycyclic rings are provided. These polycyclic nucleosides are incorporated into oligonucleotides and hybridized to complementary nucleic acid. Fluorescence spectroscopy and thermal denaturation profiles provided evidence that the polycyclic base is intercalated into the resulting duplex. The fused polycyclic ring systems optionally are substituted with reactive species which inactivate complementary nucleic acids. The oligonucleotides of this invention are useful as improved probes, diagnostic reagents, or for cleaving or derivatizing predetermined domains within nucleic acids.

19 Claims, 1 Drawing Sheet

NUCLEIC ACID INTERCALATING AGENTS

This invention relates to nucleoside derivatives and oligonucleotides containing such nucleosides. These derivatized nucleotides are capable of intercalating when incorporated into oligonucleotides and hybridized to complementary nucleic acids It was observed early that certain polycyclic aromatic compounds exhibited a strong affinity to DNA and RNA and this interaction was later attributed to intercalation (Berman et al. Ann. Rev. Biophys. Bioeng. 10:87 [1981]; Waring, Ann. Rev. Biochem. 50:159 [1981]; Peakocke, Acridines, Ackeson. Ed. Interscience Publishers: New York 1973, pp 723.758., and Gale et al., The Molecular Basis of Antibiotic Action, John Wiley & Sons: London, 1972. pp 273.306). The nature of the intercalation phenomenon has been studied by a variety of techniques and detailed geometrical information was obtained mainly from X-ray crystallographic studies of DNA-intercalator complexes (Saenger, W. Principles of Nucleic Acid Structure; Springer-Verlag: New York, 1984; pp 350–367). Letsinger first described a dinucleotide covalently linked to a phenanthridinium (Letsinger, et al.. J. Am. Chem. Soc. 103:7394 [1981]and Letsinger. et al., U.S. Pat. No. 4,547,569, [1985]) and recently a number of intercalators were synthetically attached to oligonucleotides via a linker or organic tether. The presence of the tethered intercalator was found to increase the thermal stability of the duplex that resulted from hybridization of the oligonucleotide to its complementary strand (Asseline et al. EMBO J. 3:795 [1984]; Asseline et al., J. Biol. Chem. 260:8936 [1985]; Asseline et al., Proc. Natl. Acad. Sci. USA 81:3297 [1984]; Le Doan et al., Nucl. Acids Res. 19:7749 [1987]; and Le Doan et al , Nucl. Acids Res. 15:8643 [1987]).

It is known to employ oligonucleotides or oligonucleoside derivatives having an "anti-sense" sequence in attempts to inhibit the translation of mRNA having the complementary "sense" sequence. The anti-sense sequence hybridizes to the sense mRNA in vivo, where it sterically blocks ribosomal translation of the mRNA (Zamecnik et al., Proc. Natl. Acad. Sci. USA 83.4143 [1986]; Tullis, WO 83/01451, published 1983; and Goodchild et al , WO 87/07300, published 1987).

The phosphate backbone of the anti-sense oligonucleotides has been derivatized in an effort to stabilize the polymer and make it more cell permeable (Goodchild et al., op cit [triesters]; Marcus-Sekura et Nucl. Acids Res. 15(14):5749 [1987][methylphosphonate, alkyl phosphotriesters, and phosphorothioate]; Zon et al., U.S. Ser. No. 07/030,073, filed Mar. 25, 1987, now abandoned [phosphorothioate]; and Smith et al., Proc. Natl. Acad. Sci. USA 83:2787 [1986][methylphosphonates]). Unfortunately, the kinetics of anti-sense oligonucleotide interactions with sense mRNA in vivo are not favorable for optimal therapeutic effect if one is to rely solely on hybridization of complementary bases.

The enhanced thermal stability of oligonucleotides having tethered intercalating groups has created great interest in employing such deoxyoligonucleotides as anti-sense agents. In one example, it was shown that an intercalator linked to the oligodeoxynucleotides could specifically inhibit the cytopathic effect of influenza virus in MDCK cells (Zerial et al., Nucl. Acids Res. 15:9909 [1987]) and the translation of specific mRNAs in cell-free systems (Toulme et al., Proc. Natl. Acad. Sci. USA 83:1227 [1986] and Cazenave et al., Nucl. Acids Res. 15:4717 [1987]). The presence of the tethered intercalator is desirable for therapeutic or diagnostic applications since it increases the thermal stability of the mRNA-antisense DNA duplex and reduces the rate of disassociation. However, an improved effect could be accomplished if the antisense oligomer was able to irreversibly inhibit translation. Attempts to accomplish this objective through cross. linking (Webb et al, J. Am. Chem. Soc. 108:2764 [1986]; Iverson et al., J. Am. Chem. Soc. 109:1241 [1987]) or DNA cleaving reagents (Chu et al., Proc. Natl. Acad. Sci. USA 82:963 [1985]; Dreyer et al., Proc. Natl. Acad. Sci. USA 82:968 [1985]) have been reported.

Tethering an intercalating agent to an oligodeoxynucleotide with a flexible linker is undesirable because the tethered intercalating group is free to interact with biological systems or with substances other than the target complementary nucleic acid or oligonucleotides, e.g. such cell systems as membranes and hydrophobic domains of cellular proteins such as receptors or enzymes. Similarly, tethered intercalating groups are free to avidly seek out hydrophobic surfaces in the diagnostic or therapeutic environments, for example, polyolefin lab ware and the like, where nonspecific binding will interfere in hybridization assays or therapeutic delivery of the anti-sense oligonucleotide as the case may be.

Accordingly, it is an object to provide oligonucleotides containing intercalating bases which are sterically confined.

It is another object to provide nucleosides for use in preparing such oligonucleotides.

A still further object is to provide such improved oligonucleotides which are capable of hybridizing to the complementary nucleotide sequence, thereby translationally inactivating the targeted strand. This intercalating group is rigidly confined, unlike the intercalating substituents of the art which are free to rotate and freely change their orientation.

These and other objects will be apparent from consideration of this invention as a whole.

SUMMARY OF THE INVENTION

We have determined that the objectives herein can be accomplished by fusing a substantially planar polycyclic aromatic ring system to a nucleoside base and incorporating such nucleotides into oligonucleotides. The derivatized oligonucleotides hybridize to their complementary RNA or DNA strand, the modified nucleoside remaining unpaired but nonetheless intercalated between adjacent base pairs in the duplex in a precisely stereochemically defined manner. The resulting duplex is stabilized, but since the intercalating group lacks the freedom to rotate or otherwise change its position with respect to the remainder of the molecule, other interactions aside from intercalation are minimized. The intercalating group is sterically confined by its linkage to the sugar-phosphate backbone and by the presence of one or two flanking bases.

In light of the precise steric targeting made possible by this invention, the intercalating moiety is substituted with a reactive group capable of covalently modifying a predetermined site in the complementary domain. Such reactive groups include cross-linking agents and phosphate bond cleaving agents. These reactive groups are sterically confined and less likely to interact with cellular components or nucleic acid at sites other than the target complementary sequence.

In an embodiment of the invention nucleoside derivatives that contain a substantially planar polycyclic fused base are synthesized by the novel reaction of (a) a pyridinone or pyrimidinone nucleoside substituted with a leaving group capable of participating in a nucleophilic displacement reaction and (b) an aromatic diamine. The resulting polycyclic nucleoside is incorporated into an oligodeoxynucleotide by in vitro synthesis at a predetermined specific sequence position. It was found that oligonucleotides containing an extra polycyclic base hybridize specifically to their complementary sequences and the resulting duplex shows enhanced thermal stability (depending on the context and nature of the base). These oligonucleotides therefore are useful in diagnostic or therapeutic utilities which depend upon oligonucleotide hybridization.

The novel oligonucleotides are useful as hybridization probes. The fluorescence of the polycyclic base can be followed as an integral label and detected as a measure of the presence of a complementary nucleic acid. Alternatively, the oligonucleotide is labelled by any other conventional method, e.g. by the use of a radioactive isotope of phosphorus. Nucleic acid detected by hybridization using the novel probes of this invention is diagnostically useful or may be employed in the recombinant synthesis of polypeptides.

Fluorescence Excitation Sprectrum of the Duplex

5'-CAG TGA TGT GXT
3' GTC ACT ACA C-A at Various Temperatures.

Figure 1A:
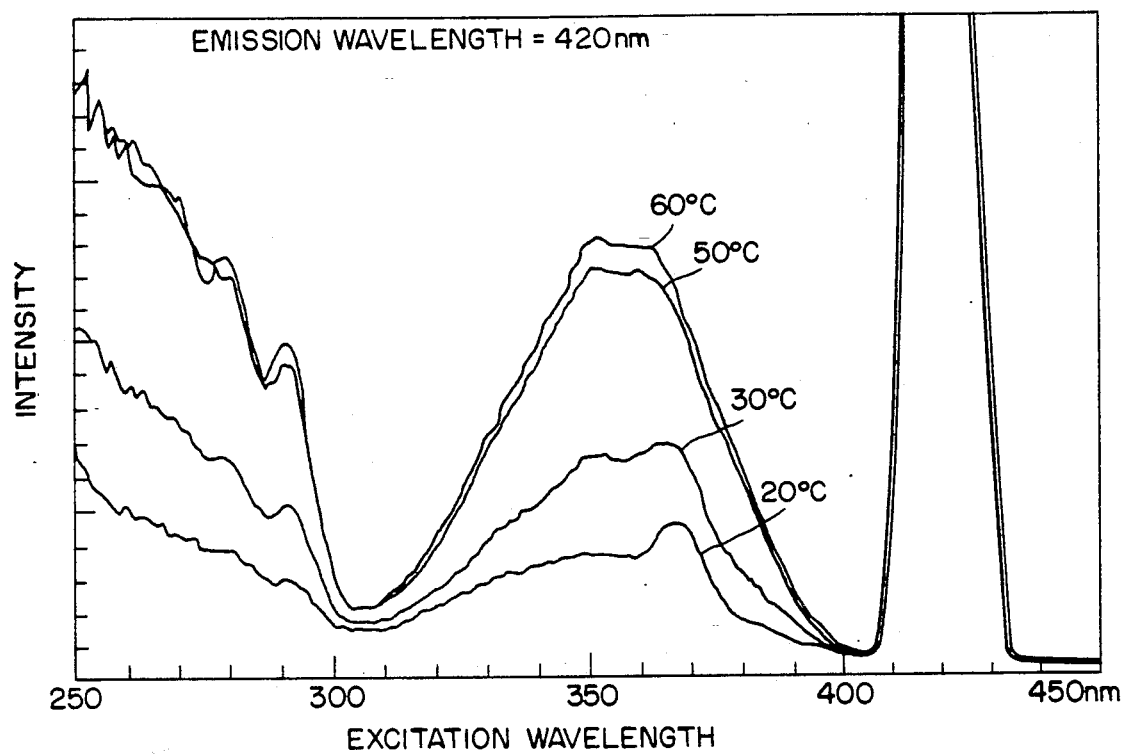
FIG. 1a depicts fluorescence quenching upon hybridization of the oligonucleotides of this invention to their complementary strand.
Figure 1B:
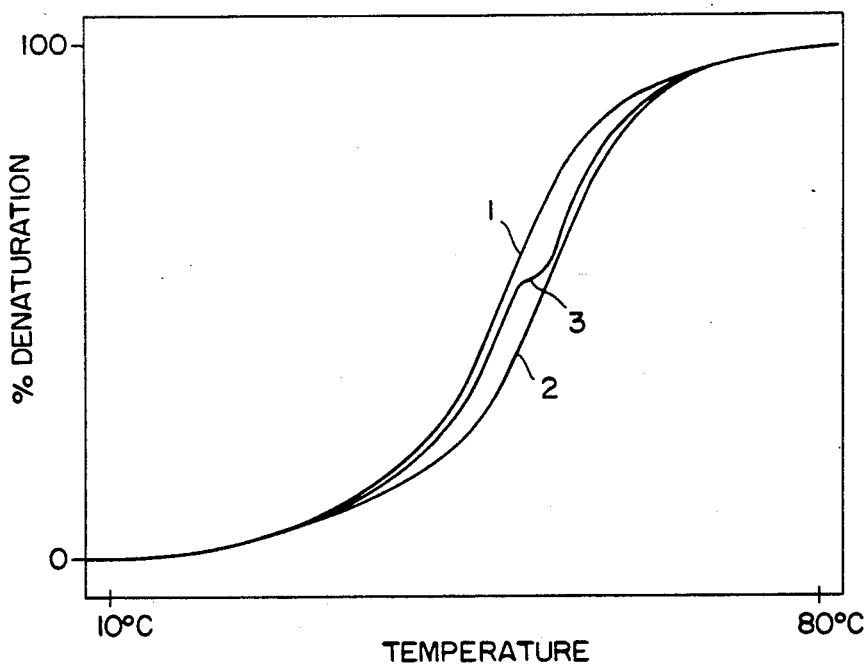

FIG. 1b shows the melting curves for duplexes containing the oligonucleotides of this invention.

Melting Curves of the Duplex

1: 5'-C-AGTG ATG TGT
3'-GXTCACTACACA

2: 5' CAG TGA TGT G-T
3' GTC ACT ACA CXT

3: 5' C-A GTG ATG TG-T
3'-GXT CAC TAC ACXA.

DETAILED DESCRIPTION OF THE INVENTION

The improved intercalating oligonucleotides of this invention have incorporated into their sequence at least one polycyclic base which is substantially planar. Substantially planar means that the steric bulk of the group lies substantially within an envelope approximating the steric gap bounded by the sugar backbone and flanking bases present in a complementary nucleic acid strand. In general, this envelope has dimensions of about 30-50 Angstroms in width and depth and about 3.7 Angstroms in thickness.

Typically, the polycyclic nucleoside will have the structure

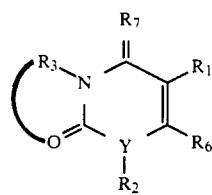

wherein $R_3$ is an aromatic polycycle, Y is C or N, $R_7$ is N or $=C(R_1)-$, $R_1$ and $R_6$ are H or a radical and $R_2$ is a ribose or deoxyribose sugar.

The key feature of this nucleoside is the presence of a fused aromatic polycycle. Since the polycycle is substantially unsaturated, it will not adopt the less planar profile of a saturated carbocycle. Further, since it is fused across the 3,4 or 1,6 positions, respectively, of the pyrimidinone or pyridinone residue, it is not free to rotate in relation to the same residue.

The structure of the aromatic polycycle is not critical so long as it is substantially hydrophobic and exhibits the desired molecular dimensions. Generally, it will contain about from 2 to 4 carbocyclic rings. However, it is also within the scope herein that the aromatic polycycle contain a heterocyclic ring, usually a nitrogen or oxygen heterocycle, and including 5 or 6-membered rings containing one nitrogen or oxygen atom. Also included herein are aromatic polycycles containing rings with substituents that do not substantially interrupt the above-described steric profile, e.g. hydroxyl, alkyl, hydroxyalkyl, carbonyl, ether or ester groups. Substituted aromatic polycycles of particular interest are quinones, especially anthraquinones. When incorporated into an oligonucleotide, anthraquinone-substituted nucleosides are useful for hydrolyzing the phosphate backbone of complementary sequences under reducing conditions (NADH) in the presence of oxygen, thus irreversibly inactivating the complementary strand. Similarly, other known reactive groups, e.g. cyanogen bromide activated methylthio, are substituted onto the aromatic polycycle. See, for example, Webb et al., Iverson et al., Chu et al., and Dreyer et al., all cited above. Hybridization results in the cross-linking of the oligonucleotide to its complementary strand.

Examples of aromatic polycycles for use herein include

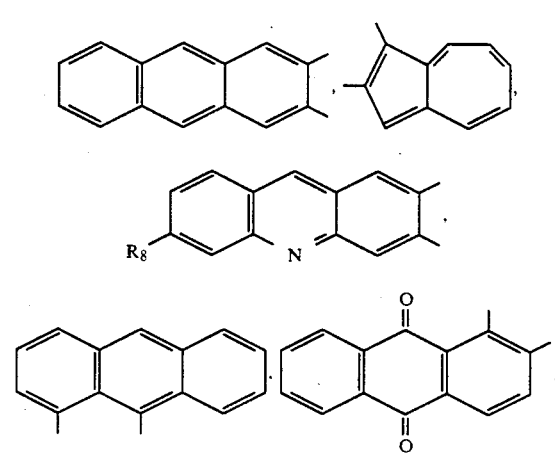

-continued

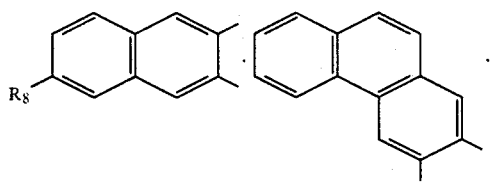

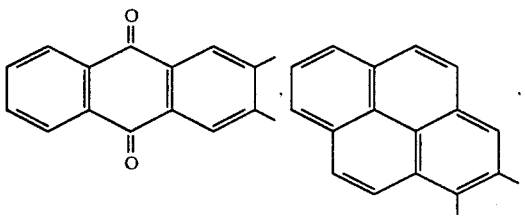

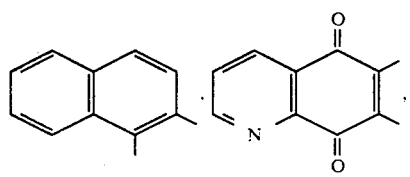

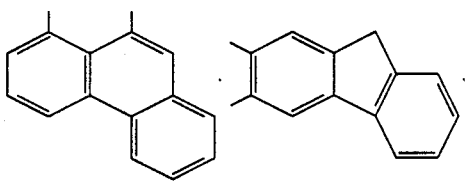

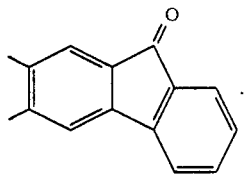

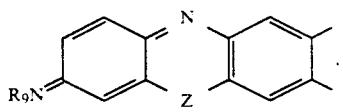

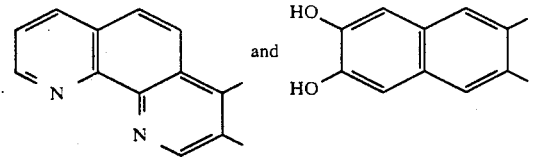

wherein $R_8 = CH_3$, $NH_2$, $N(CH_3)_2$, RCO, OH, ether, alkyl, aryl, ethylenediamine tetraacetic acid, or thioether, $R_9 = O$ or S and Z is O or S.

$R_1$ and $R_6$ are not critical substituents and in fact may be hydrogen or any radical, including halogen, ether, alkyl ether, saturated or unsaturated cycloalkyl, a heterocycle (N, S or O), hydroxyalkyl, ester, alkyl (e.g. $C_1$ to $C_{10}$), or nitro. Ordinarily useful will be the substituents found at the analogous position in known pyrimidine nucleosides, including the naturally-occurring 4-amino pyrimidine nucleosides cytosine ($R_1$ and $R_6 = H$), 5-methylcytosine ($R_1 = CH_3$, $R_6 = H$), or 5-hydroxymethylcytosine ($R_1 = CH_2OH$, $R_6 = H$). Ordinarily $R_6$ is hydrogen. For the purposes herein, neither $R_1$ nor $R_6$ are included within the calculation of the steric envelope described above.

$R_2$ is a deoxyribose or ribose sugar substituted at its anomeric carbon with the polycyclic base in either the $\alpha$ or $\beta$ configuration. Ordinarily $R_2$ is a deoxyribose. The hydroxyl groups of $R_2$ are, if necessary, substituted with appropriate blocking groups such as dimethoxy trityl in order to protect the nucleoside for synthetic methods employed for incorporation of the nucleoside into an oligonucleotide.

The above described nucleosides are produced by reacting a polycyclic aromatic diamine with a pyrimidinone or pyridinone nucleoside substituted at the 4 or 6 positions, respectively, with a leaving group. Examples of suitable leaving groups are

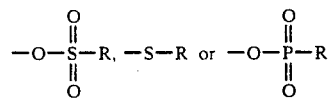

wherein R is alkyl or aryl, preferably para methyl phenyl or triisopropyl phenyl. The nucleoside starting materials are synthesized by known procedures See for example Bischofberger, Tet. Lett. 28:2821 (1987).

Nucleosides for which $R_7 = C$ can be produced by reacting an aromatic C-nucleophilic compound that has an amine or an amine precursor in an adjacent position with the same starting materials, e.g. o-Nitrophenylacetonitrile can be reacthed with the 4-substituted pyrimidine nucleoside, followed by reduction of the nitro group to give an amine and subsequent cyclization to yield the polycyclic compound.

The aromatic diamine is any of the above-described aromatic polycycles substituted with at least two amino groups, preferably on adjacent ring system carbons. Alternatively, conducting the reaction with an amine alkyl substituted aromatic polycycle will result in a fused ring containing 6 or more ring atoms. 1, 2,-diamino anthraquinone is commercially available. This is reacted with the leaving group-substituted nucleoside under basic conditions followed by acid catalyzed cyclisation in the presence of dithionite to yield the polycyclic nucleoside.

The aromatic polycyclic nucleosides of this invention then are incorporated into oligonucleotides using known procedures. The resulting oligonucleotides have the structure

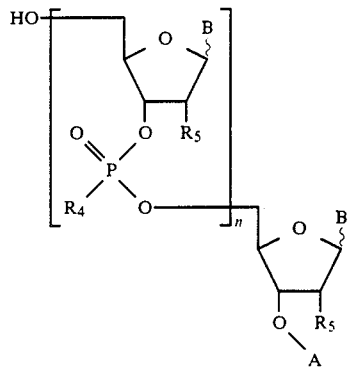

wherein A is an insoluble matrix or the nucleoside

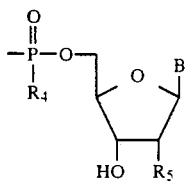

$R_5$ is H or hydroxyl, $R_4$ is O, S, alkyl, alkylamine or alkyl ether; n is an integer; and B is a base; provided, however, that at least one base is a substantially planar polycyclic base substantially having the dimensions of about 30-50 Angstroms x about 30-50 Angstroms x about 3-7 Angstroms.

The number of nucleotide bases, n, are those which are sufficient to produce an oligonucleotide that will hybridize to a complementary nucleic acid or oligonucleotide, n generally ranging about from 5 to 70. Typically, about 10 to 20 complementary bases will be sufficient to target the oligonucleotide to a unique sequence, but the number and identity of the bases will be determined by the artisan taking into account the hybridization conditions (stringent or physiologic) and the degree of discrimination desired. There is no upper limit on n although little advantage is gained with more than 50 bases in light of the synthetic burden.

The polycyclic base will be present in the nucleoside at less than 10% of the total number of bases, and such bases should not be positioned adjacent to one another. Generally, only one such base will be present in the oligonucleotide and it is best situated adjacent to either of the 5' or 3' terminal bases of the oligonucleotide. The remaining bases will be naturally occurring or, if not, they will be capable of base pairing with such natural bases.

The 5' end of the oligonucleotide may be linked to an insoluble support such as silica for the addition of more nucleosides by in vitro chemistries.

The oligonucleotides are synthesized by standard methods. e.g. enzymatic, phosphonate or phosphoramidite methods, heretofore employed to synthesize oligonucleotides.

The nucleosides of this invention are useful in manufacturing the above described oligonucleotides for antiviral utilities. The oligonucleotides are useful as analytical probes. They are labelled using an appropriate radioisotope, e.g. phosphorus 32, in the synthesis of the oligonucleotide, and the probe is used in the same way as oligonucleotide probes have been employed in the past. Certain of the polycyclic bases herein are fluorescent; this property may be assayed in order to follow hybridization and avoids the use of radioisotopes or other exogenous labels. The intercalating capability of the oligonucleotides herein permits the use of more stringent conditions. e.g. higher washing temperatures, and hence will improve the accuracy of analytical procedures and reduce background.

The reactive polycyclic substituents are analytically useful as well since it is straight-forward to follow their reaction in aqueous solution containing the target nucleic acid by electrophoretically separating the reaction products and observing for the appearance of the reaction product. Where the reactive oligonucleotide contains a phosphate cleaving group, for example the anthraquinone, then one will identify two new bands representing the split target nucleic acid. On the other hand, cross-linked nucleic acid will migrate in distinct fashion from that which has not undergone reaction.

The oligonucleotides of this invention also will have utility as agents for the anti-sense inhibition of translation of target nucleic acids. Such utilities have already been extensively explored with other anti-sense oligonucleotides and the oligonucleotides herein will be used in substantially the same fashion.

The target nucleic acids include mRNA and DNA, and may be present in restriction enzyme digests or other fragments of nucleic acids, e.g. RFLPs. mRNA also is an appropriate target nucleic acid. Nucleic acid encoding any polypeptide is a suitable target. Typically, nucleic acids encoding diagnostically or therapeutically meaningful proteins will be selected, for example viral proteins, oncogenes, growth factors, B-hemoglobin and the like. Further, other nucleic acids that encode no protein may be of interest, e.g. transcription or translation control domains or sequences useful in forensic medicine.

In the inventive method of this invention, polycyclic nucleoside derivatives are synthesized by a novel, one pot procedure. In this method, a compound (a) having the formula

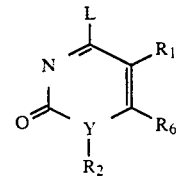

wherein L is a leaving group, $R_1$ and $R_6$ are H or a radical, Y is C or N and $R_2$ is a ribose or deoxyribose sugar, is (b) reacted with an aromatic polycyclic diamine or an aromatic C-nucleophile (e.g. cyano, convertible to the acid and decarboxylated to yield =CH—) having an amine or amine precursor in an adjacent position. For purposes herein, amine includes an amine precursor.

In a preferred embodiment, 4.0.TPS-pyrimidine nucleosides were reacted with aromatic diamines, thereby providing easy access to certain previously unknown heterocyclic ring systems (Nagarajan et al., Indian J. Chem. 8:126 [1970] and Buschauer et al., Chem. Ber. 117:2597 [1984]). The reaction is unique because two connected nucleophilic centers react with the pyrimidine nucleoside to form an extended ring system. Reactions of pyrimidine nucleosides with electrophiles are well known, e.g. reaction of cytidine and adenosine with bromoacetaldehyde yields ethenocytidine and ethenoadenosine (Leonard, N.J. CRC Crit. Rev. Biochem. 15:125 [1984] and Kusmierek et al., J. Org. Chem. 52:2374[1987]) and on reaction of cytidine with 1'-methylthiaminium salts dipyrimido[1,6-a:4',5'-d]pyrimidine derivatives are obtained (Zoltewicz et al., J. Org. Chem. 48:2481[1983]). Certain other polycyclic bases have been made from cytidine and adenosine by photochemical reactions (Inoue et al., Nucl. Acids Res. 13:7119[1985] and Shimada et al., Tet. Lett. 28:207[1987]).

The products of this novel reaction are polycyclic nucleoside derivatives. When incorporated into specific positions in oligonucleotides, they provide a model for studying intercalation related phenomena (Rebek et al., J. Am. Chem. Soc. 109:6866[1987]; Rebek et al., Ang.

Chem. Int. Ed. Eng. 26:1244 [1987]; and Herbert et al., J. Med. Chem. 30:2081[1987]) as well as useful diagnostic or therapeutic reagents. Inspection of CPG-models of a double helical DNA containing an unpaired naphth[2',3':4,5] imidazo[1,2-f]pyrimidine base reveals that the intercalated polycyclic base overlaps with the Watson-Crick hydrogen bonded cross section (Leonard et al., J. Am. Chem. Soc. 109:623[1987]). The geometry of the duplex closely resembles an acridine intercalated into a DNA duplex. Moreover, compound 11 is fluorescent and consequently provides a convenient analytical handle for diagnostic hybridization assays. An important point in the incorporation of unnatural bases into oligonucleotides by chemical synthesis on a solid support is the stability of the base to the conditions typically employed, i.e., oxidation ($I_2$/THF/$H_2O$) and deblocking (conc. $NH_4OH$/55° C.). Both monomers 19 and 20 meet that requirement. On the other hand, the highly fluorescent ethenoadenosine and ethenocytidine are known to be labile to $I_2$ (Leonard, N.J. CRC Crit. Rev. Biochem. 15:125[1984] and Kusmierek et al., J. Org. Chem. 52:2374[1987]) and would present difficulties for incorporation into oligodeoxynucleotides by chemical synthesis. The polycyclic base derived from 1,2-diaminoanthraquinone was not stable to the deblocking conditions, but deblocking could be accomplished by the usual ammonia treatment in the presence of dithionite. This notwithstanding, an alternative method for the preparation of oligomers is to employ enzymatic catalysis, e.g. polynucleotide phosphorylase (Kusmierek et al. op cit).

The monomers 21 and 22 were incorporated (Example R) into oligodeoxynucleotide sequences at different positions and contexts. We investigated the influence of the additional base on the thermal stability of the duplexes. The positional effect of an inserted naphth[2',3':4.5] imidazo[1,2-f] pyrimidine base was studied in the homooligomer duplex $A_{14}/T_{14}$ and the results are given in Table I.

TABLE I $T_m$ Data of the Homooligomer Duplexes Containing an Inserted Naphth[2',3':4.5]imidazo[1,2-f]pyrimidine Base

| Entry | Duplex | $T_m$ |
|---|---|---|
| 1 | $T_{14}/A_{14}$ | 36° C. |
| 2 | 5'-$TXT_{13}/A_{14}$ | 41° C. |
| 3 | 5'-$T_3XT_{11}A_{14}$ | 36° C. |
| 4 | 5'-$T_5XT_9/A_{14}$ | 33° C. |
| 5 | 5'-$T_7XT_7/A_{14}$ | 32° C. |
| 6 | 5'$T_9XT_5/A_{14}$ | 33° C. |
| 7 | 5'$T_{11}/XT_3/A_{14}$ | 36° C. |
| 8 | 5'-$T_{13}XT/A_{14}$ | 41° C. |

TABLE I-continued $T_m$ Data of the Homooligomer Duplexes Containing an Inserted Naphth[2',3':4.5]imidazo[1,2-f]pyrimidine Base

| Entry | Duplex | $T_m$ |
|---|---|---|
| 9 | $T_{14}/5'$-$AXA_{13}$ | 41° C. |

As can be seen, the highest stabilization resulted when the unnatural base was inserted between the two terminal base pairs as in the duplexes 5'-$TXT_{13}/A_{14}$ and 5'-$T_{13}XT/A_{14}$ (entries 2 and 8). Moving the extra base further away from the terminal base pairs reduced the amount of stabilization and the presence of the base in the middle of the duplex as in $T_7XT_7/A_{14}$ (entry 5) resulted in destabilization by 5° C. This unexpected positional effect of an inserted base finds two parallels in the literature. In one study, an acridine intercalator was attached through a linker arm of flexible length to various positions on an oligodeoxynucleotide and the greatest stabilization of the duplex was found when the linker was attached to either the 5' or 3' end and had a length of five methylene units (Asseline et al., EMBO J. 3:795[1984]; Asseline et al., J. Biol. Chem. 260:8936[1985]; Asseline et al., Proc. Natl. Acad. Sci. USA 81:3297[1984]; Le Doan et al., Nucl. Acids Res. 19:7749[1987]; and Le Doan et al., Nucl. Acids Res. 15:8643 [1987]). This best fits a model where the acridine is intercalated in the duplex between the two terminal base pairs. Another report relevant to our findings comes from an X-ray crystallographic study. Daunomycin was cocrystallized with the self-complementary oligodeoxynucleotide 5'-CGTACG and the daunomycin was found to be intercalated in the terminal CG base pairs (Quigley et al., Proc. Natl. Acad. Sci. USA 77:7204[1980]).

These results can be rationalized by taking into account the different energetic contributions of the extra base to the stability of the duplex. The presence of the additional base stabilizes the duplex due to hydrophobic and base stacking interactions. On the other hand, it causes geometric distortions to the helical structure which destabilizes the duplex. The amount of this unfavorable contribution to the duplex stability is dependent on the position of the inserted base. Being positioned close to the end, it causes less long-range distortions than in the middle. Accordingly, a polycyclic base typically is positioned within about the first 20 percent or about the last 20 percent of the length of the oligonucleotide, and ordinarily between the two 5' or 3' terminal bases.

The sequence specificity of the inserted unnatural base was studied and the results are shown in Table II.

TABLE II $T_m$ Data of the Duplexes Containing Inserted Bases $T_m$ when X =

| Entry | Duplex | | | |
|---|---|---|---|---|

TABLE II-continued

T_m Data of the Duplexes Containing Inserted Bases

| | | | | |
|---|---|---|---|---|
| 1 | 5'-CAGTGATGTGT<br>3'-GTCACTACACA | | 44.7 | |
| 2 | 5'-CXAGTGATGTGT<br>3'-G—TCACTACACA | 41.6(−2.1) | 48.4(+3.7) | 52.0(+7.3) |
| 3 | 5'-CAGTGATGTGXT<br>3'-GTCACTACAC—A | 42.3(−2.4) | 48.4(+3.7) | 51.4(+6.7) |
| 4 | 5'-C—AGTGATGTGT<br>3'-GXTCACTACACA | — | 46.0(+1.3) | 46.8(+2.1) |
| 5 | 5'-CAGTGATGTG—T<br>3'-GTCACTACACXA | — | 50.1(+5.4) | 50.6(+5.9) |
| 6 | 5'-CXAGTGATGTG—T<br>3'-G—TCACTACACXA | — | 57.1(+12.5) | 58.2(+13.5) |
| 7 | 5'-C—AGTGATGTGXT<br>3'-GXTCACTACAC—A | — | 48.2(+3.5) | 53.3(+8.6) |
| 8 | 5'-CXAGTGATGTGXT<br>3'-G—TCACTACAC—A | — | 50.6(+5.9) | — |
| 9 | 5'-C—AGTGATGTG—T<br>3'-GXTCACTACACXA | — | biphasic | — |

Duplexes containing an extra unpaired base have been studied by ¹H NMR spectroscopy and X-ray crystallography as model systems for frameshift mutagenesis (Patel et al., Biochemistry 21:445[1982]; Patel et al., Biochemistry 21:451[1982]; and Saper et al., J. Mol. Biol. 188:111[1986]). NMR studies have shown that a duplex containing an extra unpaired deoxyadenosine exists with the adenine being stacked into the duplex (Hare et al., Biochemistry 25:7456 [1986]). Thermal denaturation studies of these duplexes bearing the extra deoxyadenosine demonstrated that the presence of the extra base has a destabilizing effect on the duplex (Patel et al., supra and Saper et al., supra). It can be seen that the presence of an extra adenosine reduces the stability of the duplex by approximately 2.5° C., consistent with other findings (Zerial et al, supra). Insertion of the tetracyclic bases, on the other hand, causes a stabilization of the duplex, the pyrimido[1,6'-a]perimidine showing a higher stabilization. Clearly, context effects are present but difficult to rationalize without knowledge of the detailed geometry.

The duplexes containing two inserted bases show a peculiar phenomenon (entries 6-9, Table II). With the extra base present in opposite strands (entries 6 and 7), the duplex shows a cooperative melting curve and the amount of duplex stabilization is approximately the sum of the stabilization caused by both single insertions. When the two extra nucleotides are incorporated into the same single oligomer, however, the two inserted bases display anticooperative melting behavior and no increase in T_m is observed (entry 8) or a biphasic melting curve is obtained (entry 9, FIG. 1b). Again, these results cannot be rationalized without detailed structural information but they are suggestive of the existence of long-range changes in the helical structure caused by the presence of the extra tetracyclic base.

In an attempt to synthesize the tricyclic nucleoside derivative 3, the 4-O-TPS pyrimidine derivative 1 (Bischofberger, N. Tet. Lett. 28:2821[1987]) was treated with o-phenylenediamine in refluxing THF and a slower moving spot was observed on TLC, corresponding presumably to the adduct 2 (see below). The reaction did not stop at that stage, however, and a new fluorescent product of higher R_f formed and was isolated in 49% yield. Quite unexpectedly this product still contained Br but had lost NH₃ according to MS and elemental analyses. The λ_max in the UV spectrum was shifted to longer wavelengths relative to the starting o-phenylenediamine (λ_max=294 nm) and exhibited a well resolved vibrational structure. On the basis of these data, the product was subsequently assigned structure 4. This assignment was also confirmed by the ¹H NMR spectrum in which the signal of the H-C9 is shifted to high-field due to the anisotropy of the neighboring carbonyl group (Gunther, H. NMR-Spektroskopie; Georg Thieme Verlag; Stuttgart, 1973; pp 75-82).

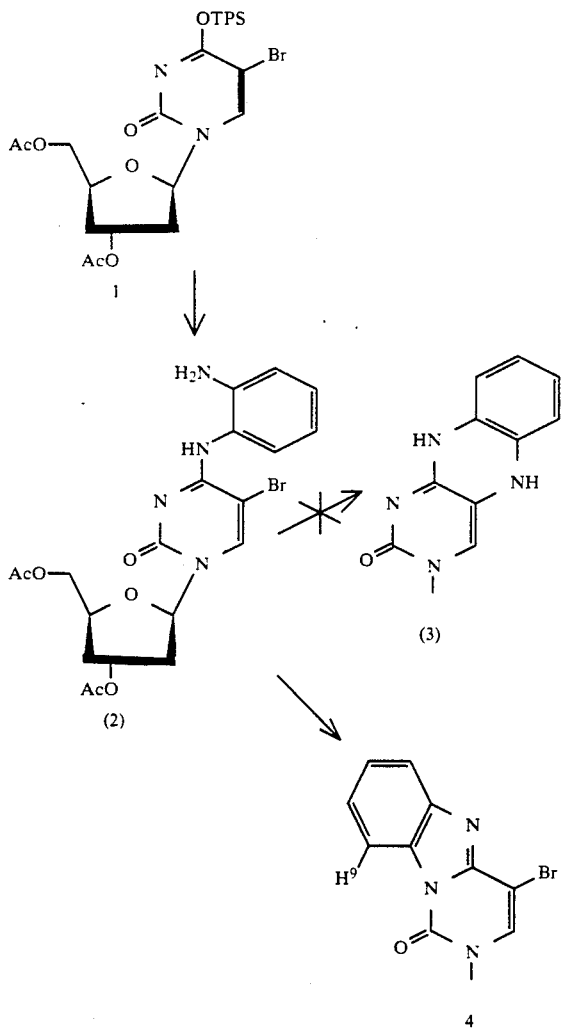

In order to examine the generality of this rather unusual reaction the 4-O-TPS-thymidine and 4-O-TPS-deoxyuridine derivatives 5, 6 and 7 were reacted with various aromatic diamines and the cyclized products 8 (from o-phenylenediamine), 10 (from 1,8-diaminonaphthalene), 11 and 12 (from 2,3-diaminonaphthalene) and the isomeric compounds 13 and 14 (from 4-nitro-o-phenylenediamine were isolated in modest to good yields in modest to good yields (see infra).

lowed by heating in acetic acid in the presence of dithionite the cyclized polycycle 23 was obtained.

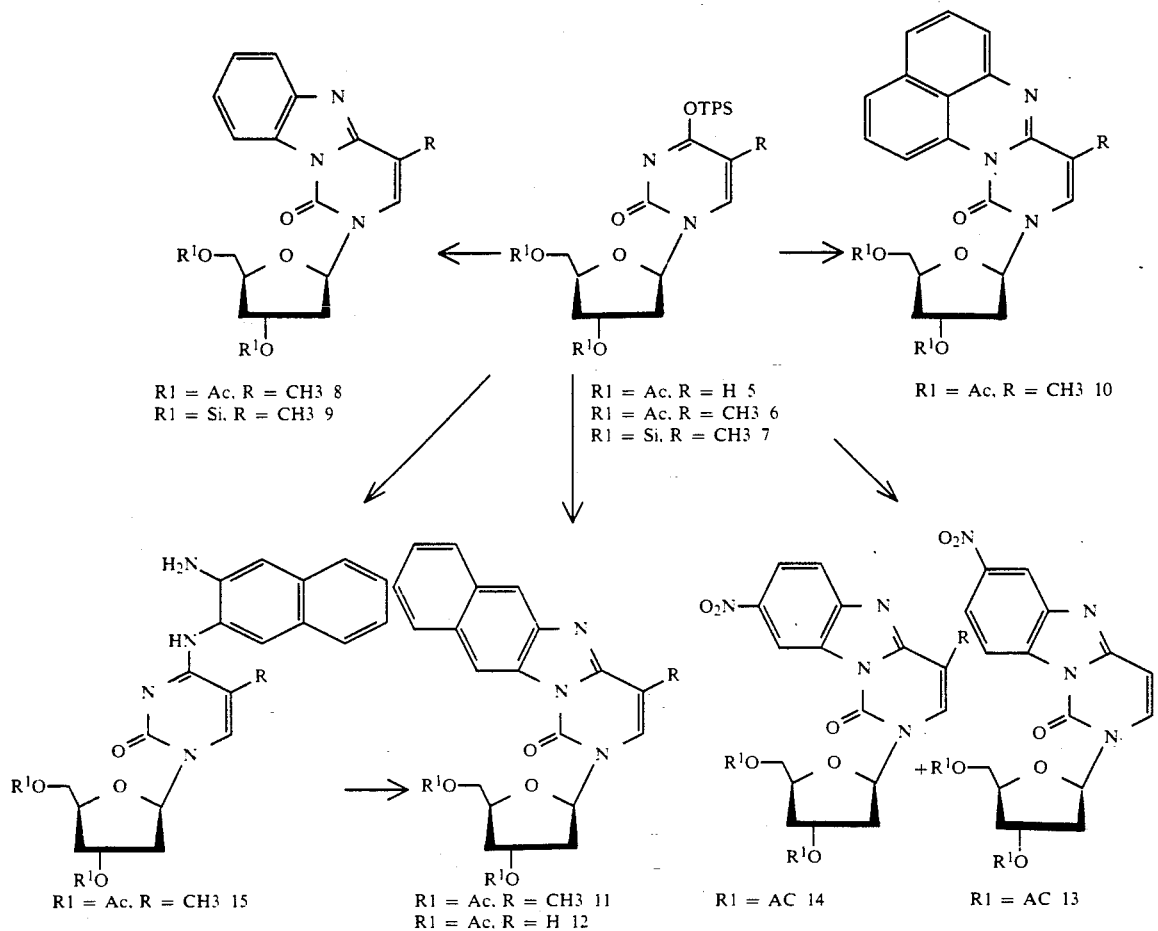

When the reaction was carried out in the presence of base none of the cyclized compounds were obtained but the reaction stopped at the intermediate stage, e.g., treatment of 6 with 2,3-diaminonaphthalene in the presence of 1 equivalent of ethyldiisopropylamine yielded 15 in 60% yield. 15 was slowly converted to 11 in refluxing THF, more rapidly in the presence of acetic acid demonstrating that this second cyclization step is acid catalyzed.

Alternatively, the reaction was carried out in two steps by first treating the 4-O-TPS derivative with the diamine in the presence of base and then affecting the cyclization with acid. By treating o-phenylenediamine and 7 with potassium hexamethyldisilazane in THF at −78° C., work up and subsequent reflux of the crude product in THF in the presence of 0.8 equivalents of acetic acid the cyclized product 9 was obtained in 60% overall yield. Similarly, by treating 7 and 1,2-diaminoanthraquinone with potassium hexamethyldisilazane in THF, work-up and subsequent treatment of the crude mixture with tetrabutyl ammonium fluoride fol-

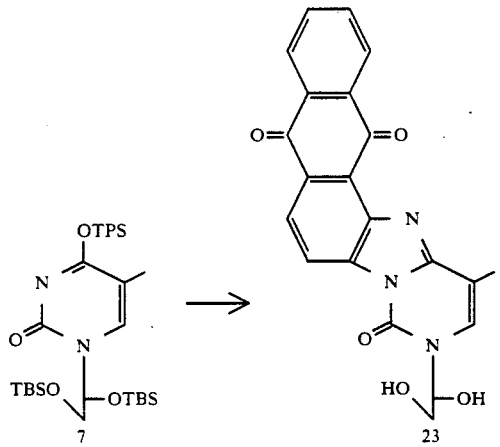

On the other hand, reaction of 7 with ethylene diamine and of 6 with 2,3-diaminopyridine led only to the adducts 16 and 17, respectively, which could not be cyclized under a variety of reaction conditions.

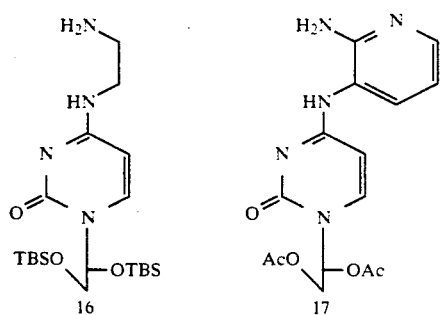

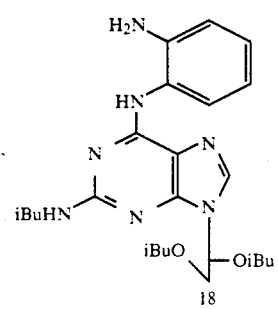

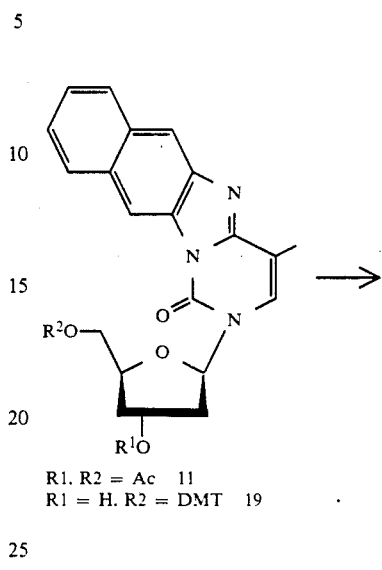

R1, R2 = Ac   11
R1 = H, R2 = DMT   19

Also attempts to extend this reaction to purine nucleosides failed. The reaction of o-phenylenediamine with N², 3 ,5'-triisobutyryl-6-O-TPS-dG resulted only in the formation of 18 which did not undergo any cyclization.

Without being limited to any particular theory of operation, a possible mechanism of this novel cyclization is shown below.

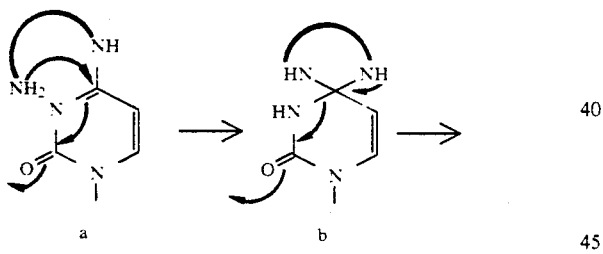

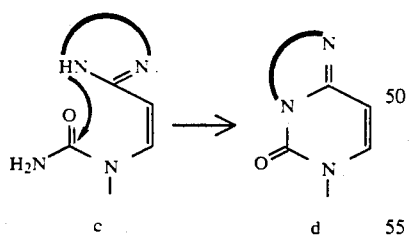

It might involve initial Michael addition of the primary amine in a to form b, followed by ring opening (b>c) and cyclization with los of NH$_3$ to give the cyclized product (c>d).

10 and 11 on treatment with conc. NH$_3$ rapidly gave the deacetylated derivatives which proved to be stable to further ammonia treatment at 55° C. as observed on TLC and were directly dimethoxytritylated (DMT-Cl/pyridine) yielding 19 and 20 and subsequently converted to the phosphonate triethylammonium salts 21 and 22. 21 and 22 were then incorporated into oligonucleotides using the standard H-phosphonate protocol (Froehler et al., Tet. Lett. 27:469[1986] and Froehler et al., Nucl. Acids. Res. 14:5399 [1986]).

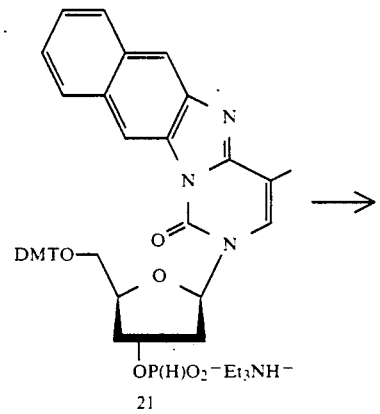

5'-CXAGTGATGTGT
5'-CAGTGATGTGXT
5'-ACACATCACTXG
5'-AXCACATCACTG
5'-CXAGTGATGTGXT
5'-AXCACATCACTXG

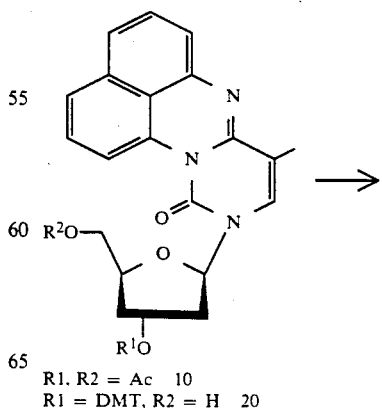

R1, R2 = Ac   10
R1 = DMT, R2 = H   20

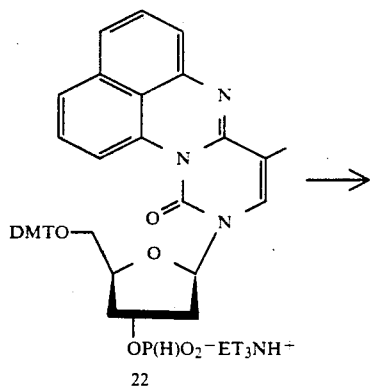

22

5'-CYAGTGATGTGT
5'-CAGTGATGTGXT
5'-ACACATCACTXG
5'-AXCACATCACTG

The oligomers obtained after deblocking were purified by gel electrophoresis and desalted by reversed phase chromatography using a $C_{18}$ Sep pack column. The presence of the tetracyclic bases in the oligomers was confirmed by UV and fluorescence spectroscopies. The amount of fluorescence quenching in the single stranded oligomers containing the fluorescent naphth[2',3':4,5]imidazo[1,2-f]pyrimidine ring system was determined by snake venom phosphodiesterase digest and was found to be approximately 50%.

EXAMPLES

2'-Deoxyuridine and thymidine were purchased from Sigma Chemical Co.; all other reagents were purchased from Aldrich Chemical Co. $^1$H NMR spectra were obtained using an 80 MHz IBM NR/80 spectrometer and recorded as ppm ($\delta$) using TMS as an internal standard. Mass spectra were obtained using the positive-ion fast-atom-bombardment (FAB) technique on a Hewlett-Packard 5985C instrument. UV spectra were obtained on a Beckman UV-7 spectrophotometer using methanol as the solvent. Fluorescence spectra were obtained using an SLM 8000C spectrofluorometer. For thin layer chromatography (TLC) EM DC-Alufolien Kieselgel-60 $F_{254}$ plates were used; column chromatography was performed with EM Kieselgel-60 (70-230 mesh). Melting points were determined on a Buchi 510 capillary melting point apparatus and are uncorrected. Elemental analyses were done by Chemical Analytical Services, University of California, Berkeley, Calif. Oligonucleotides were synthesized on a Biosearch Model 4000 DNA synthesizer.

EXAMPLE A

3',5'-Di-O-acetyl-4-O-(2,4,6-triisopropylphenylsulfonyl)-2'-deoxy-5-bromo uridine (1). From 3',5'-diacetyl-5-bromo-2'-deoxyuridine (4.628 g, 11.8 mmol) 1 was obtained according to the published procedure (Bischofberger, supra) as white crystals after chromatography (ether/hexane 1:1 to 1:0) and recrystallization from ether (5.0 g, 85%): mp 116–120° C.; $^1$H NMR $\delta$8.18 (s, H-C6), 7.21 (s, 2 aromatic H), 6.09 (dxd, $J_1$=6.4, $J_2$=5.6, anomeric H), 5.08– 5.28 (m, H-C3'), 4.01–4.50 (m, 3 H), 3.13–2.50 (m, 5H), 2.11, 2.08 (2 s, 2 $H_3$CCO), 1.18–1.39 (m, ~18 H). Anal. ($C_{28}H_{37}BrN_2O_9S$) C, H, N, Br.

EXAMPLE B

3',5'-Di-O-acetyl-4-O-(2,4,6-triisopropylphenylsulfonyl) thymidine (6). From 3',5'-diacetylthymidine (2.82 g, 8.6 mmol) 5 was obtained according to the published procedure (Bischofberger supra) as white crystals after recrystallization from $CH_2Cl_2$/ether) (3.78 g, 74%): mp 127-130 C; $^1$H NMR $\delta$7.76 (s, 1 H), 7.20 (s, 2 H), 6.12 (dxd, $J_1$=8.0, $J_2$=5.8, anomeric H), 5.06-5.27 (m, 1 H), 4.01-4.54 (m, 3 H), 2.47-3.11 (m, 5 H), 2.06, 2.07 (2 s, 2 $H_3$CCO, $H_3$C-C5), 1.15-1.40 (m, ~18 H). Anal. ($C_{29}H_{40}N_2O_9S$) C, H, N.

EXAMPLE C

3',5'-Di-O-acetyl-4-O-(2,4,6-triisopropylphenylsulfonyl)-2'-deoxy uridine (5). From 3',5'-diacetyl-2'-deoxy uridine (3.03 g, 9.7 mmol) 5 was obtained according to the published procedure (Bischofberger supra) as a foam after chromatography ($CH_2Cl_2$/ethyl acetate 20:1 to 5:1) (3.43 g, 61%): $^1$H NMR $\delta$8.02 ($\delta$, J=7.3, H-C5), 6.11 (t, J=7.6, anomeric H), 5.08-5.29 (m, H-C3'), 4.04-4.46 (m, 3 H), 2.63-3.11 (m, 5 H), 2.08, 2.05 (2 s, 2 $H_3$CCO), 1.15-1.40 (m, ~18 H). Anal. ($C_{28}H_{38}N_2O_9S$) C, H, N.

EXAMPLE D

4-Bromo-2-(3,5-di-O-acetyl-2-deoxy-1$\beta$D-ribofuranosyl)-pyrimido[1,6-a]benzimidazole-1(2 H)-one (4). A solution of 3',5'-diacetyl-4-O-triisopropylphenylsulfonyl-5-bromo-2'-deoxy ruidine (1) (178 mg, 0.36 mmol) and o-phenylenediamine (51 mg, 0.47 mmol) in THF (3 mL) was heated to reflux for 16 h. Removal of the solvent and purification of the crude product by preparative TLC (ethyl acetate/$CH_2Cl_2$ 1:3) yielded 4 as a foam which crystallized on addition of methanol (79 mg, 49%): mp 70–72° C.; $^1$H NMR $\delta$8.31-8.49 (m, H-C9), 7.76-8.01 (m, 2 H), 7.38-7.58 (m, 2 H), 6.61 (dxd, $J_1$=8.5, $J_2$=6.1, anomeric H), 5.22-5.41 (m, 1 H), 4.29-4.51 (m, 2 H), 2.34-2.85 (m, 2 H), 2.22, 2.14 (2 s, 2 $H_3$CCO); UV (0.96 mg in 25 mL): $\lambda_{max}$ 224 (18,100), 240 (10,800), 284 (4,800), 292 (6,000), 307 (7,500), 317 (9,000), 330 (5,800); $\lambda_{min}$ 265 (3,000); MS 466, 464 (2, MH+), 266, 264 (85). 81 (100). Anal. ($C_{19}H_{18}BrN_3O_6$) C, H, Br, N.

EXAMPLE E

4-Methyl-2-(3,5-di-O-acetyl-2-deoxy-1$\beta$D-ribofuranosyl)-pyrimido[1,6-a]benzimidazole.1(2 H)-one (8). A solution of 3',5'-diacetyl-4-O-TPS-thymidine (339 mg, 0.57 mmol) and o-phenylenediamine (8 mg, 0.81 mmol) in THF (5 mL) was heated to reflux for 16 h. The mixture was poured into $CH_2Cl_2$ ($^{18}$ 200 mL) and extracted with 1 M citric acid solution to remove excess o-phenylenediamine. Concentrating the organic layer and chromatography of the crude product ($CH_2Cl_2$/ethyl acetate 5:2 to 0:1) gave 8 as a foam (193 mg, 84%) which crystallized upon addition of methanol as the methanol adduct: mp 78° C.; $^1$H NMR $\delta$8.58-8.32 (m, H-C9), 7.16-7.99 (m, 4 H), 6.65 (dxd, $J_1$=8.8, $J_2$=5.6, anomeric H), 5.20-5.41 (m, 1 H), 4.30-4.50 (m, 3 H), 3.49 (d, $CH_3$OH), 2.42 (d, J=1.2, $H_3$C-C4), 2.18, 2.16 (2 s, 2 $H_3$CCO), 2.10-2.80 (m, 2 H); UV (1.66 mg in 50 mL); $\lambda$max 235 sh (15,900), 280 (11,400), 290 (13,800), 302 sh (114,900), 310 (17,500), 322 (11,400); $\lambda_{min}$ 260 (6,000); MS 400 (10, MH+), 200 (100). Anal. ($C_{20}H_{21}N_3O_6$) C, H, N.

EXAMPLE F

5-Methyl-3-(3,5-di-O-acetyl-2-deoxy1-βD-ribofuranosyl)-pyrimido [1,b-a]perimidine-2(3H)-one (10). A solution of 1,8-diaminonaphthalene (120 mg. 0.76 mmol) and 3',5'-di-O-acetyl-4,-OOTPS-thymidine (343 mg. 0.58 mmol) in THF (5 mL) was heated to reflux for 24 h. Purification of the crude reaction mixture by chromatography ($CH_2Cl_2$/methanol yielded 10 as yellow needles (205 mg, 78%): mp 158° C.; $^1$H NMR δ8.14 (dxd, $J_1$=2.4, $J_2$=8.8, anomeric H), 5.12–5.32 (m, H-COCO), 4.15–4.43 (m, 3 H), 2.0–2.75 (m, 2 H), 2.10, 2.13 (2 s, 2 $H_3$CCO), 2.00 (d, J=0.8. $H_3$C-C2); UV (1.75 mg in 25 mL); $\lambda_{max}$ 456 sh (900), 438 sh (2400), 404 (3,600), 380 (3,700), 342 sh (8,500), 332 (12,800), 324 sh (9,600), 284 (7.600); $\lambda_{min}$ 294 (5,400), 266 (5,900). Anal. ($C_{24}H_{23}N_3O_6$) C, H, N.

EXAMPLE G 2-(3,5-Di-O-acetyl-2-deoxy-1-βD-ribofuranosyl)-naphth[2',3':4,5]imidazo[1,2 f]pyrimidine-1(2H)-one (12). A solution of 3',5'-di-O-acetyl-4-O-TPS-2'-deoxyuridine 5 (317 mg. 0.548 mmol) and 2,3-diaminonaphthalene (105 mg, 0.66 mmol) in THF (3 mL) was heated to reflux for 16 h. After work-up ($CH_2Cl_2$/), chromatography of the crude reaction mixture ($CH_2Cl_2$/ethyl acetate 1:1 to 0:1) and recrystallization of the fluorescent product from $CH_2Cl_2$/methanol 12 obtained as white crystals (138 mg, 58%): mp 83–88° C.; $^1$H NMR δ8.84, 8.22 (2 s, 2 H), 7.90–8.17 (m, 2 H), 7.62–7.37 m, 3 H), 6.67 (d, J=8.1, HOC3), 6.58 (t, J=5.9, anomeric H). 2.15 (s, 2 $H_3$CO); UV (1.12 mg in 50 mL); λmax 375 (5,400), 358 (10,500), 346 (12,600), 331 (9,700), 287 (37,000), 276 (31,000). 265 (20,900), 243 (26,400); λmin 296 (2,900), 282 (16,300), 269 (17,500), 260 (18,200), 228 (17,900): MS 436 (MH+, 8), 236 (80). Anal. ($C_{23}H_{21}N_3O_6$; methanol complex) C, H, N.

EXAMPLE H

4-Methyl-2-(3,5-di-O-acetyl-2-deoxy-1βD-ribofruatnosyl)-napth [2',3':4,5]imidazo[1,2-f]pyrimidine (11). A solution of 2,3-diaminonaphthalene (180 mg, 1.14 mmol) and 3',5'-di-O-acetyl-4-O-TPS-thymidine (6) (464 mg, 0.78 mmol) in THF (5 mL) was heated to reflux for 16 h. The reaction mixture was diluted with $CH_2Cl_2$ (~200 mL) and extracted with 1 M citric acid solution to remove excess 2,3-diaminonaphthalene. The organic layer was concentrated and the crude product purified by chromatography ($CH_2Cl_2$/ethyl acetate 1:1 to 0:1) and recrystallized from methanol/$CH_2Cl_2$ yielding 11 as white crystals (231 mg, 66%): mp 128–130° C.; $^1$H NMR δ8.86 (2 s, 2 H), 7.90–8.17 (m, 2 H), 7.36–7.62 (m, 2 H), 7.28 (m, 1 H), 6.63 (dxd, $J_1$=8.0, $J_2$=6.4, anomeric H), 5.18–5.41 (m, 1 H), 4.23–4.50 (m, 3 H), 2.40 (d, J=1.6, $H_3$C-C4), 2.16, 2.15 (2 s, 2 $H_3$CCO) 2.0 0 2.70 (m 2 H) UV (0.64 in 25 mL); $\lambda_{max}$ 372 (4,500), 352 (9,700), 348 (10,000), 340 (3,700), 288 (24,200), 278 (19,500), 268 sh (13,900), 244 (25,800); $\lambda_{min}$ 300 (2,400), 283 (13,100), 272 (11,800); MS 450 (6, MH+), 250 (100). Anal. ($C_{24}H_{23}N_3O_6$) C, H, N.

EXAMPLE I

4-Methyl-2-(3,5-di-O-(tert-butyldimethylsilyl)-λ-2-deoxy-1βD-ribofuranosyl)-pyrimido[1,6-a]benzimidazole-1(2H)-one (9). To a solution of 3',5'-bis-O-(tert-butyldimethylsilyl)-4-O-TPS-thymidine (7) (401 mg, 0.54 mmol) and o-phenylenediamine (76 mg, 0.70 mmol) in THF (10 mL) was added potassium hexamethyldisilazane (1.1 mL of a 0.5 M solution in toluene, 0.55 mmol) at −78° C. After 5 min the reaction mixture was quenched (saturated $NH_4Cl$ solution) and worked up in ether. The crude reaction product was dissolved in THF and heated to reflux with acetic acid (40 μL. 0.40 mmol) for 8 h. The reaction mixture was concentrated and the product purified by preparative TLC (ether/hexane 2:1) yielding the fluorescent 9 as a foam (175 mg. 60%): $^1$H NMR δ8.36–8.57 (m, H-C9), 7.75–7.95 (m, 1 H), 7.32–7.62 (m, 3 H), 6.65 (dxd, $J_1$=7.8, $J_2$=6.2, anomeric H), 4.36–4.60 (m, 1 H), 3.77–4.12 (m, 3 H), 2.38 (s, $H_3$C), 1.89–2.54 (m, $H_2$C2'), 1.75–2.05 (m, ~18 H), 0.05–0.22 (m ~12 H); UV (1.18 mg in 25 mL): $\lambda_{max}$ 220 (27,600), 236 sh (15,000), 280 (10,600). 290 (12,600), 300 (13,500), 310 (16,100), 323 (10,600); $\lambda_{min}$ 260 (5,700), 284 (10.300). 295 (12,000), 320 (10,300); MS 544 (MH+, 2), 200 (100).

EXAMPLE J

4-Methyl-7-nitro-2-(3,5-di-O-acetyl-2-deoxy-1-βD-ribofuranosyl)-pyrimido [1,6-a]benzimidazole-1(2H)-one (13) and 4-methyl-8nitro-2-(3,5-di-O -acetyl-2-deoxy-1-βD-ribofuranosyl)-pyrimido[1,6-a]benzimidazole-1(2 H)-one (14). A solution of 3', 5'-di-O-acetyl-4-TPS-thymidine (1.231 g, 2.08 mmol) and 4-nitro-o-phenylenediamine (420 mg. 2.74 mmol) in THF (10 mL) was heated to reflux for 48 h. The mixture was diluted with $CH_2Cl_2$ (150 mL) and extracted with 1 M citric acid solution (3×50 mL). The organic layer was concentrated and the crude mixture purified by chromatography ($CH_2Cl_2$/ethyl acetate 5:1 to 0:1) yielding 2 fractions. From the faster eluting fraction 13 was obtained as a powder after recrystallization from $CH_2Cl_2$/methanol (300 mg, 32%); the slower eluting fraction yielded 14 as yellow needles after recrystallization from $CH_2Cl_2$/methanol (397 mg. 43%). The structure was assigned on the basis of the low field shift of the H-C9 signal in the $^1$H NMR spectrum due to the anisotropy of the carbonyl oxygen. 13: mp 100–103° C.; $^1$H NMR δ9.32 (d, J=1.2, H-C9), 8.41 (dxd, $J_1$=9.3, $J_2$1.2,H-C7), 7.89 (d, J=9.3, H-C6), 7.43 (s, broad, H-C3), 6.60 (t, J=6.6, anomeric H), 5.20–5.44 (m, 1H), 4.29–4.58 (m, 3H), 1.99–2.88 (m, 2 H), 2.42 (s, broad, $H_3$C-C4), 2.17 (s, 2 $H_3$CCO); UV (2.02 mg in 75 mL): $\lambda_{max}$ 350 (15,800, 272 (11,500); $\lambda_{min}$ 296 (4,900), 255 (10,500); 14: mp 85–90° C.; $^1$H NMR δ8.74 (d, J=1.5, H-C6), 8.58 (d, J=8.8, H-C9), 8.34 (dxd, $J_1$=1.5$J_2$=8.8, H-C8), 7.39 (s, broad, H-C3), 6.62 (dxd, $J_1$=6.3, $J_2$=8.4, anomeric H). 5.22–5.45 (m, 1 H), 4.28–4.58 (m, 3 H), 2.00–2.87 (m, $H_2$C), 2.45 (s, broad, $H_3$C-C4), 2.19 (s, 2 $H_3$CCO); UV (1.53 mg in 75 mL): $\lambda_{max}$ 330 sh (5,600). 282 (23,900), 236 (12,600); MS 445 (MH+, 3), 245 (25).

EXAMPLE K 3,5'-Di-O-acetyl-5-methyl-4N-(2-amino-3-naphthyl)-2'-deoxycytidine (15). A solution of 3', 5'-di-O-acetyl-4-O-TPS-thymidine (203 mg, 0.34 mg); 2,3-diaminonaphthalene (75 mg, 0.47 mmol) and ethyl diisopropylamine (100 μl, 0.57 mmol) in THF (3 mL) was refluxed for 24 h. Chromatrgraphy (ethyl acetate/methanol 1:0 to 10:1) of the crude product mixture yielded 15 as a foam (76 mg. 47%): $^1$H NMR δ7.71–7.13 (m, 6 H), 6.96 (s, 1 H), 6.29 (dxd. $J_1$=5.6, $J_2$=8.0, anomeric H), 5.08–5.32 (m, H-C3'), 4.12–4.42 (m, 3 H), 2.66–2.0 (m, 2 H-C2'), 2.12, 2.08 (2 s, 2 $H_3$CCO), 2.02 (s, broad, $H_3$C-C5); UV (0.75 mg in 25 mL): $\lambda_{max}$ 240 (31,700), 282 (16,100), 340 sh (440), end absorption to 380; $\lambda_{min}$ 262 (13,700); MS 467 (18, MH+), 267 (100), 250 (50).

EXAMPLE L

4-Methyl-2-(5-O-dimethoxytrityl-2-deoxy- 1βD-ribofuranosyl)-napth [2',3':4,5]imidazo[1,2-f]pyrimidine-1(2H)- one (19). To a solution of 11 (54 mg, 0.12 mmol) in dioxane ( mL) was added conc.aqu.NH$_3$ (3 mL). After 5 h the deacetylation was complete according to TLC and the solution was evaporated to dryness. The residue was dissolved in pyridine (5 mL) and DMT-Cl (140 mg, 0.47 mmol) was added batchwise over a period of 24 h. The reaction was quenched by addition of methanol, evaporated and the product purified by thick layer chromatography (CH$_2$CL$_2$/ethyl acetate 5:1); the fluorescent band was eluted with ethyl acetate yielding pure 19 as a yellow foam (60 mg. 75%): $^1$H NMR δ8.88, 8.23 (2 s, 2 H), 8.15-7.90 (m, 2 H), 7.80-6.60 (m, ~1 7 H), 4.55-4.80 (m, 1 H), 4.0-4.27 (m, 1 H), 3.3-3.8 (m, 2 H), 3.75 (s, 2 H$_3$CO), 2.30 -2.67 (m, 2 H$_2$C2'), 1.95 (s, broad, H$_3$C-C4).

EXAMPLE M

1-Methyl-3-(5-O-dimethoxytrityl-2-deoxy-1-βD-ribofuranosyl)-pyrimido[1,6-a]perimidine-2(3H)-one (20). To a solution of the diacetyl compound 10 (116 mg, 0.26 mmol) in THF (3 mL)/methanol (2 mL) was added 38% aqu.NH$_3$ (2 mL) and the resulting mixture was left at ambient temperature for 24 h. The solvents were removed, the solid residue evaporated 2× from pyridine (5 mL), finally dissolved in pyridine (5 mL) and DMT-Cl (156 mg. 0.46 mmol) was added. After 2 days the mixture was quenched by addition of methanol (0.5 mL). concentrated to dryness and the residue purified by preparative TLC (CH$_2$Cl$_2$/ethyl acetate 5:1). The yellow band was collected yielding 20 as a yellow foam (133 mg. 76%): $^1$H NMR δ8.17 (dxd, J$_1$=6.6, J$_2$=1.9, H-C5), 6.72-7.57 (m, ~19 H), 6.41 (t, J =7.0, anomeric H), 4.41-4.63 (m, 1 H). 3.93-4.12 (m, 1 H), 3.78 (s, 2H$_3$CO). 3.34-3.54 (m, 2 H), 2.22-2.49 (m, 2 H). 1.65 (s, broad, H$_3$C-Cl).

EXAMPLE N

5-O-Dimethoxytrityl-2-deoxy-1β-(4-methyl-1-oxo-2-(2H)-naphth [2',3':4,5]imidazo[1,2 f]pyrimidinyl)-3-O-ribofuranosylphosphonate triethylammonium salt (21). To CH$_2$Cl$_2$ (10 mL) was sequentially added at −78° C.: N-methyl morpholine (2 mL), PCl$_3$ (200 μl) and 1,2,4-triazole (860 mg). The mixture was stirred at room temperature for 1 h, recooled to −78° C. and a solution of 16 (135 mg, 0.20 mmol) in CH$_2$Cl$_2$ (8 mL) was added. The reaction mixture was allowed to warm to ~0° C., quenched by addition of H$_2$O, diluted with CH$_2$Cl$_2$ (150 mL) and extracted 2× with 1 M biethylammoniumbicarbonate solution pH 7.5. The organic layer was dried (MgSO$_4$), concentrated, the solid residue treated with ethyl acetate, the insoluble part tris-(triethylammonium-phosphonate) removed by filtration, the filtrate concentrated and the crude product purified by preparative TLC (CH$_2$Cl$_2$)/methanol/triethylamine 100:10:1). The fluorescent band was collected and eluted yielding 21 as white foam (141 mg, 84%): $^1$H NMR δ10.78 (s, NH), 8.89, 8.24 (2×, 2 H). 6.67-8.17 (m, ~19 H), 5.10 9m, 1 H), 4.37 (m, 1 H), 3.77 (s, 2 H$_3$CO), 3.40 (m, 2 H), 3.09 (qua, J=7.3, ~6 H), 2.50-2.80 (m, 2 H), 1.82 (d, J ~1, H$_3$C-C5), 1.39 (t, J=7.3, ~9 H).

EXAMPLE O

5-O-Dimethoxytrityl-2-deoxy-1β-(5-methyl-2-oxo(2H) benzo[d,e]pyrimido[1,6-a]perimidine-2yl)-3-O-ribofuanosyl phosphonate triethylammonium salt (22). To CH$_2$Cl$_2$ (10 mL) was sequentially added at −78° C.: N-methyl morpholine (1 mL), PCl$_3$ (150 μl) and triazole (720 mg). The mixture was stirred at ambient temperature for 1 h, and a solution of 18 (105 mg. 0.157 mmol) in CH$_2$Cl$_2$ (3 mL) was added at −78 C. After warming to ~0° C., the reaction was quenched by addition of H$_2$O, diluted with CH$_2$Cl$_2$ (100 mL) and extracted 2× with 1 M ammoniumbicarbonate solution pH 7 5. The organic layer was dried concentrated and the residue dispersed in ethyl acetate. The insoluble material (ammonium phosphonate) was removed by filtration, the filtrate concentrated and the residue purified by preparative TLC (CH$_2$Cl$_2$/methanol/triethylamine 100:10:1) yielding 22 as a yellow foam (83 mg, 63%): $^1$H NMR δ8.16 (dxd, J$_1$=6.8,J$_2$=1.9, H-C5), 6.68-7.56 (m, ~19 H), 6.50 (dxd, J$_1$=7.9, J$_2$=5.9, anomeric H), 4.83-5.16 (m, broad, 1 H), 4.17 -4.38 (m, 1 H), 3.78 (s, 2H$_3$CO), 3.36-3.55 (m, 2 H), 3.06 (qua, J=7.1, 6 H), 2.41-2.64 (m, 2 H), 1.51 (s, broad, H$_3$C-Cl), 1.33 (t, J=7.1~9H).

EXAMPLE P

2 Isobutyrylamino-6-(2-amino-phenylamino)-9-(3,5-bis-O-isobutyryl-2-deoxy-1βD-ribofuranosyl)-purine (18). A solution of N2,03',05'-triisobutyryl-2'-deoxy-6.0-TPS-guanosine $^{21}$ (175 mg, 0.23 mmol) and o-phenylenediamine (100 mg, 0.92 mmol) in THF (3 mL) was heated to reflux for 24 h. The crude product was purified by chromatography (ethylacetate)/CH$_2$Cl$_2$ (1:5 to 1:0) yielding 22 as a foam (103 mg, 76%): $^1$H NMR δ7.95 (s, broad, 1 H), 7.77 (s, H-C8), 6.61-7.37 (m, ~4 H), 6.25 (dxd, J$_1$=8.1, J$_2$=6.1, anomeric H). 5.25-5.45 (m, 1 H), 4.13-4.43 (m, ~3 H), 2.30-3.14 (m, ~5 H), 0.88-1.24 (m, ~18 H); UV (2.73 mg in 100 mL): ~$_{max}$ 230 (21,500), 292 (12,100), end absorption to 360; λ$_{min}$ 262 (10,800); MS 568 (MH+, 4), 312 (100), 242 (35), 225 (52).

EXAMPLE O

5.Methyl-2'-deoxy-3',5'-bis-O-(tert-butyldimethyl-silyl)-4-N-(2-amino-3-pyridyl) cytidine (17). A solution of 3',5'-bis-O-(tert-butyldimethylsilyl)-4-O-TPS-thymidine 7 (115 mg. 0.15 mmol) and 2,3-diaminopyridine (100 mg. 0.92 mmol) in THF (2 mL) was heated to reflux for 18 h. The crude reaction mixture was purified by preparative TLC (ether/hexane 4:1), the yellow band was collected and eluted with ether yielding 17 as a foam (40 mg, 47%): $^1$H NMR δ7.74 (dxd, J$_1$=4.8, J$_2$=0.9, H-C6"), 6.99 (dxd, J$_1$=8.0, J$_2$=0.9, H-C4"), 6.80 (dxd, J$_1$=8.0, J$_2$=4.8, H-C5"), 6.40 (dxd, J$_1$=6.5, J$_2$=6.0, anomeric H), 4.30-4.54 (m, 1 H), 3.74-4.00 (m, 3 H), 2.02 (s, H$_3$C), 1.92-2.45 (m, H$_2$C2'), 0.78-1.05 (m, ~18H), 0.05-0.22 (m. ~12 H); UV (1.03 mg in 25 mL): λ$_{max}$ 286 (12,500), 370 (16,400), end absorption to 440: λ$_{min}$ 252 (8,500), 315 (4,200); MS 562 (MH+, 2), 218 (100).

EXAMPLE R

Oligonucleotide Synthesis. Polymer bound nucleotide H-phosphonates were prepared as previously described (Froehler et al., Tet. Let. 27:469[1986]) on control pore glass using the DBU salts of the protected nucleoside H-phosphonates. For introducing the polycyclic nucleosides, a solution of ~25 mg of the triethylammonium salts 21 and 22, respectively in 1 mL pyridine/acetonitrile 1:1 was used in the automated synthesis. For efficient coupling the wait time in the programmed coupling step for 21 and 22 was increased from 6×8 sec to 26×8 sec. After oxidation and deblocking, the fragments were purified by polyacrylamide gel electrophoresis and the fluorescent (in the case of 17) or yellow (in the case of 19) bands were eluted and the eluate desalted by loading onto a reversed phase $C_{18}$ SepPac column (Waters Associates), washing with $H_2O$ and finally eluting the fragments with 25% aqueous acetonitrile.

EXAMPLE S

Fluorescence Studies. Addition of the complementary undecamer 5'-ACACATCACTG to the fluorescent 5'-CAG TGA TGT GXT dodecamer caused a decrease in the fluorescence intensity whereas addition of random DNA sequences to the fluorescent dodecamer had no effect, proving that the fluorescence intensity decrease is specific to the complementary oligomer. Also the fluorescence intensity did not further change after one equivalent of the complementary strand had been added, thus indicating the formation of a duplex. The fluorescence intensity could be increased to the original level on heating as shown in FIG. 1a, consistent with the thermal denaturation of the duplex. The other dodecamers containing the naphth[2',3':4,5]imidazo[1,2f]pyrimidine base gave similar results, with varying levels of fluorescence quenching. Other bases within the scope herein are useful in similar fashion for the assay of hybridization, which as shown is readily followed by changes in fluorescence of the oligonucleotide. Such changes may include changes in fluorescence intensity (quenching or enhancement), wavelength (emission or adsorption), and the time course of fluorescence (energy transfer).

EXAMPLE T

Thermal Denaturation Profiles. The melting curves of the duplexes containing one or two of the tetracyclic bases derived from monomers 21 and 22, respectively, were measured at 2 mM oligomer concentration in buffered solution (100 mM NaCl, 10 mM $Na_2HPO_4$, 1 mM EDTA, pH=7.5). For comparison and reference, the melting profiles of the corresponding duplexes containing no extra bases and of the duplexes containing an extra adenosine were also measured. From these melting curves, the $T_m$ of the duplexes were determined and the results are depicted in Tables I and II and FIG. 1b.

EXAMPLE U

Hypochromicity measurements. Hypochromicities of the duplexes were measured at 260 nm with a Kontron Uvikon 810 spectrophotometer in a 1 cm masked cuvette. The samples were 100 mM NaCl, 10 mM $Na_2HPO_4$, 1 mM EDTA at pH 7.2 and contained the oligomers at a concentration of 2 μM in a total volume of 1 mL. The extinction coefficients (ξ) of the oligomers were calculated and the ξ of the oligomers containing the excra tetracyclic bases were approximated by adding the values of the ξ of the monomers at 260 nm (for 10:ξ (260)=15 mL/μmol; for 11:ξ(260)=6 mL/μmol) to the ξ of the oligomers devoid of the tetracyclic bases. The samples were degassed with He, heated to −55° C. for 4 h, allowed to cool and maintained at 0° C. overnight. The absorbance of the samples was monitored from 15° C. to ~80° C., increasing the temperature at a rate of 0.2° C./min. Each sample was measured at least twice and the data were separately normalized to % denaturation (% denaturation=100% $[A_o-A_i]/[A_f-A_i]$, where $A_o$= observed abs, $A_i$=initial abs, $A_f$=final abs.) and combined to obtain a melting curve. A linear least squares analysis of this data gave a slope of transition and y-intercept from which the $T_m$ values were calculated.

EXAMPLE V 3-(3,5-Di-O-acetyl-2-deoxy-1-βD-ribofuraranosyl)-4-methyl-anthr [1',2':4,5]imidazo[1,2-f]pyrimidine-2,8,13(3H)-trione 23: To a solution of 1,2-diamino anthraquinone (400 mg. 1.68 mmol) and 7 (1.155 g; 1.54 mmol) in THF (20 ml) was added a solution of Potassium hexamethyl disilazane (0.5 M; 3.1 ml., 1.6 mmol) at −78° C. The solution was allowed to warm to room temperature and was subsequently worked up and chromatographed ($SiO_2$; $CH_2Cl_2$/hexane/ethyl acetate 30:10:4 to 30:10:13). The TLC-pure fractions were collected yielding 512 mg of a dark red foam. A solution of the foam obtained above (317 mg; 0.47 mmol) in THF (5 ml) was stirred with tetrabutyl ammonium fluoride (2 5 ml of a 1 M solution in THF) for 1 hr. The mixture was concentrated and purified by chromatography ($SiO_2$; $CH_2Cl_2$/THF 3:1 to 0:1). The TLC pure fractions were collected yielding 150 mg of a red powder. The powder was dissolved in THF (2 ml)/acetic acid (2 ml)/$H_2O$ (1.5 ml) and stirred at 50° C. overnight in the presence of dithionite (200 mg). The mixture was evaporated to dryness yielding 550 mg of a yellow compound. In order to increase the solubility of the product, part of the yellow material (59 mg) was treated with acetic anhydride (0 5 ml)/pyridine (2.5 ml) for 18 hr The reaction was quenched (methanol), worked up and the crude product chromatographed by prep. TLC ($CH_2Cl_2$/ethyl acetate 3:1) yielding a yellow, fluorescent powder (15 mg). $^1$H-NMR. 8.8 (d, J=8 1H), 8.1-8.4 (m, ~4H) 7.5-7.9 (m, ~3H), 7.50 (m, 1H), 6.5 (dxd $J_1$=6, $J_2$=8, 1H), 5.2 (m, 1H) 4.4 (m, ~3H), 2.5 (d, J=1, 3H), 2.1 (s, ~6H), 1.9-2.8 (m).

We claim:

1. A pyridinone or pyrimidinone nucleoside comprising a fused aromatic polycyclic base having molecular dimensions equal to or less than about 30–50 angstroms by about 30–50 angstroms by about 3–7 angstroms, wherein the nucleoside is represented by the structure

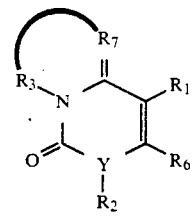

wherein
$R_3$ is an aromatic polycycle comprising up to four fused aromatic rings;
Y is C or N;
$R_7$ is N or $=C(R_1)-$;
$R_1$ and $R_6$ are independently selected from the group consisting of H, halogen, $C_1$-$C_{10}$-alkyl, saturated or unsaturated cycloalkyl, $C_1$-$C_{10}$-alkylcarbonyloxy, $C_1$-$C_{10}$-alkyl, hydroxy-$C_1$-$C_{10}$-alkyl, heterocycle (N,O, or S), and nitro and;
$R_2$ is a ribose or deoxyribose sugar.

2. The nucleoside of claim 1 wherein Y is N.

3. The nucleoside of claim 2 wherein $R_3$ is selected from the group of

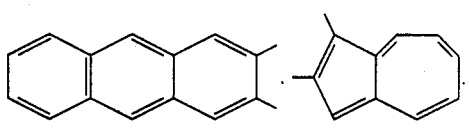
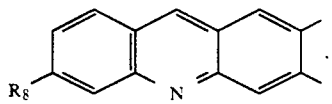
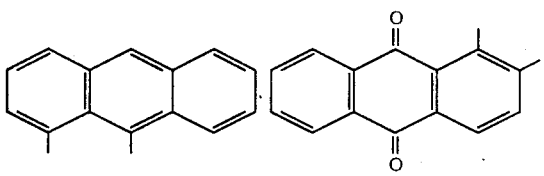
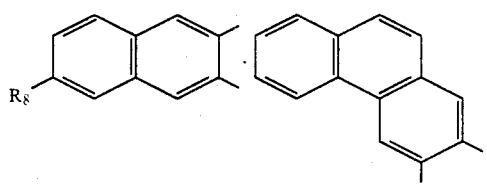
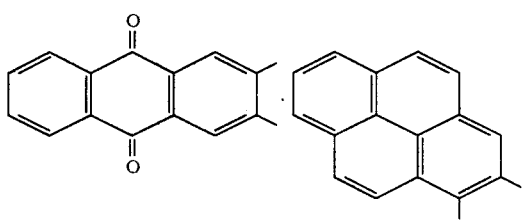
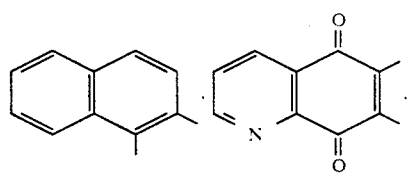
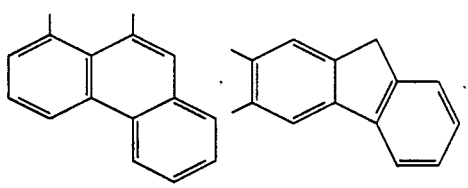
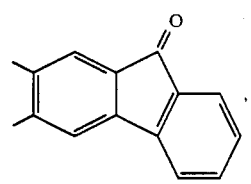
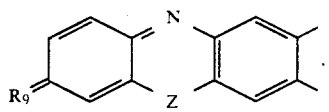

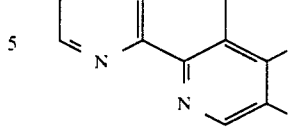
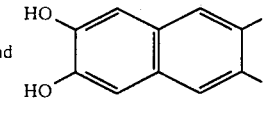

-continued and wherein $R_8$=$CH_3$, $NH_2$, $N(CH_3)_2$, RCO, OH, $C_1$-$C_{10}$-alkoxy, $C_1$-$C_{10}$-alkyl, $C_6$-$C_{12}$-aryl, ethylenediamine tetraacetic acid, or thioether, $R_9$=S, and Z is O or S.

4. The nucleoside of claim 1 wherein $R_3$ is the residue of an aromatic polycyclic ring containing from 2 to 4 cycloalkylene rings.

5. The nucleoside of claim 1 wherein the aromatic polycycle is completely unsaturated.

6. The nucleoside of claim 1 wherein the aromatic polycycle contains one or more substituents selected from the group oxo, hydroxyl, thio-$C_1$-$C_{10}$-alkyl, amino, $C_1$-$C_{10}$-alkylamino, formyl, $C_1$-$C_{10}$-alkoxy, $C_1$-$C_{10}$-alkylcarbonyl, $C_6$-$C_{12}$-aryl, and ethylenediamine tetraacetic acid.

7. The nucleoside of claim 1 wherein the aromatic polycycle comprises a heterocyclic ring containing O, S or N.

8. The nucleoside of claim 1 wherein the aromatic polycycle comprises a quinone.

9. The nucleoside of claim 8 wherein the aromatic polycycle comprises an anthraquinone.

10. The nucleoside of claim 4 wherein the cycloalkylene rings contain from 4 to 7 carbon atoms.

11. The nucleoside of claim 1 wherein $R_1$ is cyclic or acyclic alkenyl, or halogen.

12. The nucleoside of claim 1 wherein $R_1$ is methyl, $C_1$-$C_{10}$-alkoxy, or hydrogen.

13. An oligonucleotide of the structure:

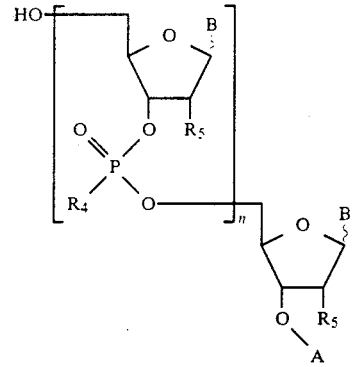

wherein A is an insoluble matrix or the nucleoside

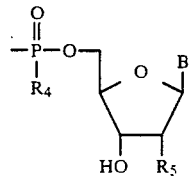

$R_5$ is H or hydroxyl; $R_4$ is O, S, alkyl, alkylamine, or alkyl ether; n is an integer; and B is a nucleoside base; wherein at least one base is of the structure;

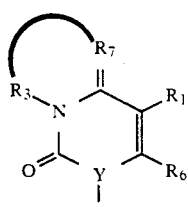

and is positioned within about the first 20 percent or about the last 20 percent of the length of the oligonucleotide, and wherein R$_3$ is the residue of an aromatic polycycle;
Y is C or N;
R$_7$ is N or =C(R$_1$)—;
R$_1$ and R$_6$ are independently selected from the group consisting of hydrogen, halogen, C$_1$–C$_{10}$-alkoxy, saturated or unsaturated cycloalkyl, C$_1$–C$_{10}$-alkyl-carbonyloxy, C$_1$–C$_{10}$-alkyl, hydroxy-C$_1$–C$_{10}$-alkyl, heterocycle (N,O,S), and nitro.

14. The oligonucleotide of claim 13 wherein the bases are guanidine, cytosine, adenosine, uracil, or thymine.

15. The oligonucleotide of claim 13 wherein n ranges about from 5 to 70.

16. The oligonucleotide of claim 13 wherein the polycyclic aromatic base is present in the second nucleoside 5′ or 3′ from the end of the oligonucleotide.

17. The oligonucleotide of claim 13 wherein the polycyclic aromatic base is fluorescent.

18. The oligonucleotide of claim 13 wherein the polycyclic aromatic base is

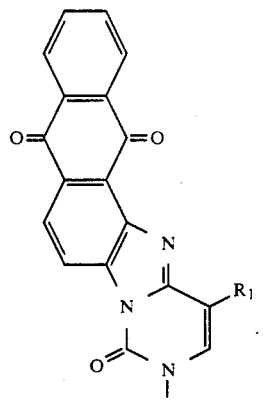

19. The compound of claim 13 wherein R$_3$ is in substantially the same plane as the group

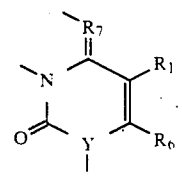

* * * * *